United States Patent
Wagner et al.

(10) Patent No.: US 6,565,566 B1
(45) Date of Patent: May 20, 2003

(54) SACRAL SCREW ASSEMBLY AND METHOD

(75) Inventors: Erik J. Wagner, Austin, TX (US); Ralph F. Rashbaum, Dallas, TX (US)

(73) Assignee: Spinal Concepts, Inc., Austin, TX (US)

( * ) Notice: Subject to any disclaimer, the term of this patent is extended or adjusted under 35 U.S.C. 154(b) by 0 days.

(21) Appl. No.: 09/532,387

(22) Filed: Mar. 22, 2000

(51) Int. Cl.[7] .............................................. A61B 17/70
(52) U.S. Cl. ........................................ 606/61; 606/73
(58) Field of Search ............................. 606/61, 60, 72, 606/73

(56) References Cited

U.S. PATENT DOCUMENTS

| | | | |
|---|---|---|---|
| 4,950,269 A | * 8/1990 | Gaines, Jr. ................ | 606/61 |
| 5,147,363 A | 9/1992 | Härle .......................... | 606/73 |
| 5,242,252 A | 9/1993 | Härle ......................... | 411/311 |
| 5,259,398 A | * 11/1993 | Vrespa ....................... | 606/65 |
| 5,474,555 A | * 12/1995 | Puno et al. .................. | 606/73 |
| 5,544,993 A | 8/1996 | Härle .......................... | 411/414 |
| 5,562,663 A | 10/1996 | Wisnewski et al. .......... | 606/61 |
| 5,591,165 A | 1/1997 | Jackson ....................... | 606/61 |
| 5,630,817 A | * 5/1997 | Rokegem et al. ............ | 606/61 |
| 5,643,269 A | 7/1997 | Härle .......................... | 606/79 |
| 5,653,710 A | 8/1997 | Härle .......................... | 606/73 |
| 5,716,355 A | 2/1998 | Jackson et al. .............. | 606/61 |
| 5,720,751 A | 2/1998 | Jackson ....................... | 606/86 |
| 5,738,685 A | * 4/1998 | Halm et al. .................. | 606/61 |
| 5,743,914 A | 4/1998 | Skiba .......................... | 606/73 |
| 5,776,135 A | 7/1998 | Errico et al. ................. | 606/61 |
| 5,785,711 A | 7/1998 | Errico et al. ................. | 606/61 |
| 5,810,819 A | 9/1998 | Errico et al. ................. | 606/61 |
| 5,961,518 A | 10/1999 | Errico et al. ................. | 606/61 |
| 5,989,250 A | 11/1999 | Wagner et al. ............... | 606/61 |
| 5,997,539 A | 12/1999 | Errico et al. ................. | 606/61 |
| 6,017,344 A | 1/2000 | Errico et al. ................. | 606/61 |
| 6,030,389 A | 2/2000 | Wagner et al. ............... | 606/71 |

OTHER PUBLICATIONS

Jackson, "The 'Sacroiliac Buttress' Intrasacral Fixation and Translation–Rotation Force Application With Spinal Intrumentation," Spine & Scoliosis Surgery, The North Kansas City Hospital, 4 pgs.

Edwards, "Spondylolisthesis: Reduction and Fixation," Jun. 1993, 6 pgs.

Excerpts from Edwards, "Reconstruction of Acute Lumbar Injury," Operative Techniques in Orthopaedics, vol. 1, No. 1, Jan. 1991, 9 pgs.

Ruland et al., "Triangulation of Pedicular Instrumentation," Spine, vol. 16, No. 6 Supplement, 1991, pp. S270–S275.

(List continued on next page.)

*Primary Examiner*—Cary E. O'Connor
(74) *Attorney, Agent, or Firm*—Meyertons, Hood, Kivlin, Kowert & Goetzel, P.C.; Eric B. Meyertons

(57) ABSTRACT

A sacral screw assembly may provide a connection to a sacrum for a spinal fixation assembly. The sacral screw assembly may include a fixation component, connector, spinal rod, and a fastener. The connector and fixation component are configured to interconnect so that the connector inhibits translational and rotational motion of a spinal rod that is positioned within an opening of the connector. The connector may include a flared arm tip. The flared arm tip may fit within a groove of the fixation component to help position the connector within a cavity of the fixation component. The flared arm tip may also inhibit passage of the connector through the top of the cavity. The fixation component may have a threaded shank. The threaded shank may have a coarse pitch section located near a head of the fixation component, and a fine pitch section located near an end of the shank. When the fixation component is inserted into a sacrum, the coarse pitch section of threading and the fine pitch section of threading may inhibit backout of the fixation component from the sacrum.

64 Claims, 6 Drawing Sheets

OTHER PUBLICATIONS

Doh et al., "Acute Sciatica from Sacral Screw Impingement on the Lumbosacral plexus: Emphasis on the Safe Zones for Sacral Screw Placement," 1 pg.

Danek™ Surgical Technique Manual, "TSRH™ Spinal Implant System," pp 1–16.

Henstorf et al., "Transpedicular Fixation of Spinal Disorders with Steffee Plates," reprinted from Surgical Rounds for Orthopaedics, Mar. 1987, 4 pgs.

Exceprts from Steffee et al., "Reduction and Stabilization of Grade IV Spondylolisthesis," © 1988 by J. B. Lippincott Company, 4 pgs.

Code, "New Fastener Thread Design," Fastener Technology International, vol. 17, No. 4, Aug. 1994, pp. 80–81.

Stuart Spine Group, Compact CD Low Back, Surgeons Technical Monograph, © 1994, 56 pgs.

"Pedicle Screws—General Info," Sep. 1998, 3 pgs.

Maric et al., "Instrumentation for Posterior Fixation of the Thoracic and Lumbar Spine," BNI Quarterly, vol. 10, No. 1, 1994, pp. 18–26.

Sofamor, "Transverse Link Device (DLT)," © 1993, 1 pg.

Sofamor, "DLT Set," © 1993, 1 pg.

Sofamor, "Compact CD, Low Back," © 1993, 6 pgs.

* cited by examiner

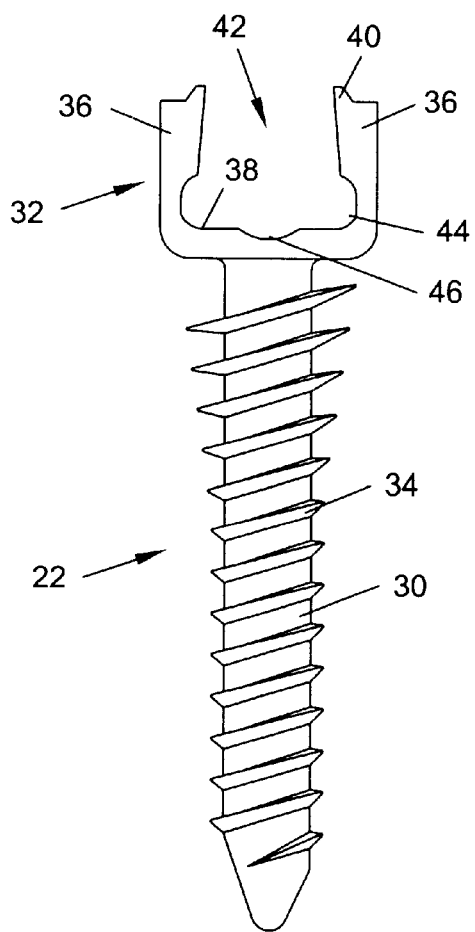
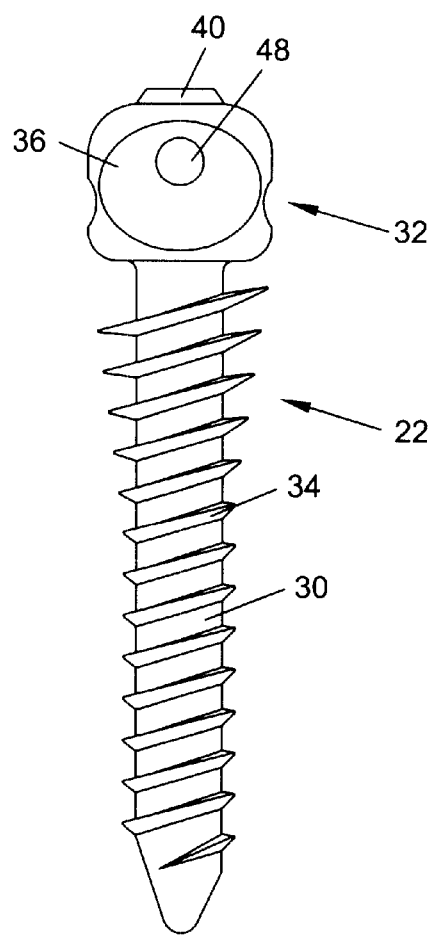
FIG. 2a      FIG. 2b
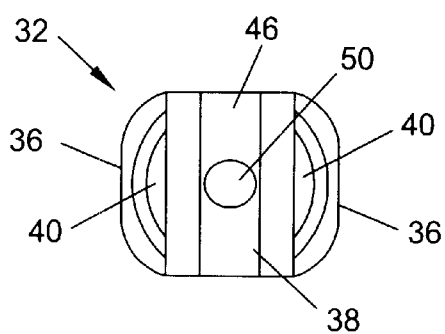
FIG. 2c

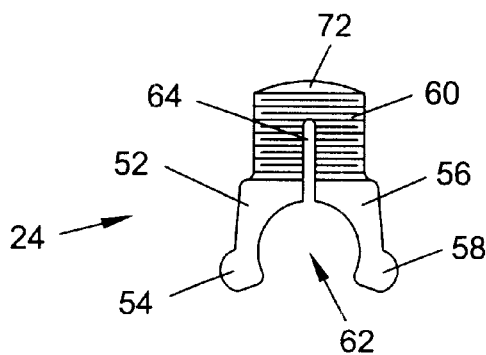
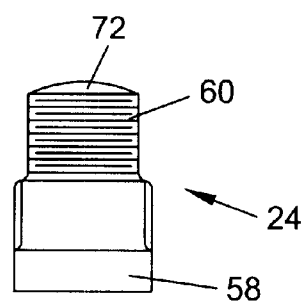
FIG. 3a  FIG. 3b
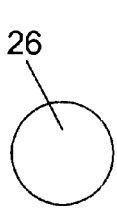
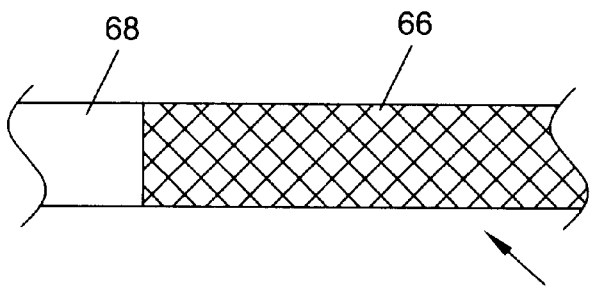
FIG. 4a  FIG. 4b
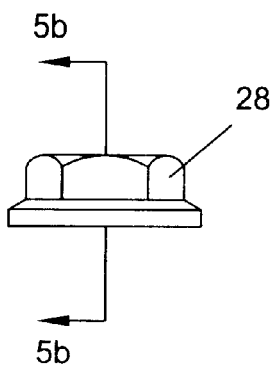
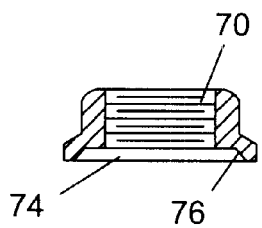
FIG. 5a  FIG. 5b

SACRAL SCREW ASSEMBLY AND METHOD

BACKGROUND OF THE INVENTION

1. Field of the Invention

The present invention generally relates to spinal fixation systems and the like. An embodiment of the present invention relates to a sacral screw used during procedures for stabilizing a human spine.

2. Description of the Related Art

Spinal fixation procedures, such as lumbar sacral fusion and the correction of spinal deformities such as scoliotic curves, are well known and frequently used medical procedures. Pedicle, lateral, and oblique mounting devices may be used to secure corrective spinal instrumentation to a portion of the spine that has been selected to be fused by arthrodesis.

A spinal fixation system typically includes corrective spinal instrumentation that is attached to selected vertebrae of the spine by screws, hooks, and clamps. The corrective spinal instrumentation includes spinal rods or plates that are generally positioned parallel to the patient's back. The corrective spinal instrumentation may also include transverse connecting rods that extend between neighboring spinal rods. Spinal fixation systems may be used to correct problems in the lumbar and thoracic portions of the spine. Spinal fixation systems may be installed posterior to the spine on opposite sides of the spinous process and adjacent to the transverse process.

Various types of screws, hooks, and clamps have been used for attaching corrective spinal instrumentation to selected portions of the patient's spine. Examples of screws and other types of attachments are illustrated in U.S. Pat. Nos. 4,763,644; 4,805,602; 4,887,596; 4,950,269; 5,129,388; and 5,743,914. Each of these patents is incorporated by reference as if fully set forth herein.

Spinal fixation procedures that involve fixation of the sacrum may be difficult. Sacral fixation procedures that require long constructs, and/or sagittal plane realignment or revision may be particularly troublesome. Also troublesome are sacral fixation procedures in patients who have weak bone. Some of the problems associated with sacral fixation procedures are the difficult anatomy of the area; the poor bone quality frequently found in the sacrum; and the large lumbosacral loads and cantilever pullout forces applied across the region. The bone quality of the sacrum may be poor even in patients who do not have weak bone.

One sacral fixation procedure involves the insertion of spinal rods into the sacrum. The procedure is described in a paper titled:"The 'Sacroiliac Buttress' Intrasacral And Translation-Rotation Force Application With Spinal Instrumentation," by Roger P. Jackson, M.D., and is incorporated by reference as if fully set forth herein.

SUMMARY OF THE INVENTION

A sacral screw assembly that may include a spinal rod, a fixation component, a connector, and a fastener. The fixation component may have a top section and a shank. The top section may have a cavity defined by a base and two walls. The cavity may narrow in a direction from the base toward a top of the cavity. The base may have a rod groove that complements the shape of the spinal rod and enables the sacral screw assembly to have a low profile above the sacrum during use. The fixation component may include indentations in the outer surfaces of the walls. An indentation may allow instrumentation to properly position a connector within a cavity of a fixation component. Upper ends of walls of the fixation component may form semi-circular or arcuate wedges.

The shank of the fixation component may have a variable diameter and a tapered end. The diameter of the shank may be widest at a location on the shank adjacent to the upper section of the fixation component. Alternatively, the shank may have a constant width and a tapered end. The shank may be threaded. The outer diameter of the thread may widen as the thread approaches the upper section of the fixation component. In another embodiment, the spinal fixation component has two flights of thread. The first thread extends from a position near the end of the shank to a position near the upper section of the fixation component. The second thread begins near the end of the shank, but the thread terminates a significant distance below the base. The combination of two flights of threads on the shank produces a fine pitch thread section and a coarse pitch thread section. The fine pitch thread section provides good purchase in dense bone material, and the coarse pitch thread section provides good purchase in less dense bone material. The combination of a fine pitch thread section and a coarse pitch thread section may provide the bone screw with increased resistance to thread backout.

The connector may include an upper section and a lower section. A portion of the upper section of the connector may be threaded. A threaded section of the fastener may engage the thread of the connector to secure the connector to the fixation component during use. The bottom of the fastener may have a ring that engages the wedges on the fixation component. The ring and wedges may ensure that the connector is properly positioned within the fixation component. The ring and wedges may also prevent the walls of the fixation component from flaring outwards when the fastener attaches a connector to the fixation component. The top of the connector may be rounded so that the top of the connector generally conforms to the shape of the fastener when the fastener attaches the connector to the fixation component. A rounded top of the connector may ensure that no sharp edges are present at the interface between the connector and the fastener when the fastener attaches the connector to the fixation component.

The lower section of the connector may include two arms that define an opening. A spinal rod may be inserted into the opening of the connector. A slot may be located in the upper section of the connector between the two arms. The slot may allow the arms to be deflected relative to each other. When the slot narrows, the arms apply a compressive force against a rod positioned in the opening to securely hold the rod. When the slot widens, a rod positioned within the opening may be positioned or removed from the opening.

The connector may be configured to be at least partially disposed within the cavity of the fixation component during use. The inner surfaces of the cavity walls may exert a compressive force onto outer surfaces of the connector. The compressive force exerted on the outer surfaces of the connector may serve to narrow the slot in the upper section of the connector. Narrowing the slot may inhibit movement of a spinal rod positioned within the opening of the connector. The surface of the spinal rod to which the connector attaches and/or surfaces of the opening, may be textured to further reduce the possibility of movement of a spinal rod positioned within the opening.

The arms may have flared portions at the ends of the arms. The cavity of the fixation component may have grooves configured to receive the flared portions of the arms. The flared portions of the rods may allow for the easy placement of a connector within the cavity of a fixation component. The flared portions of the rods may also inhibit displacement of the connector through the top of the cavity prior to securing the connector to the fixation component with the fastener. An outer surface of one or both of the arms of the connector may taper to complement the narrowing of the cavity from the base to the top of the cavity. The surfaces of the cavity walls and/or outer surfaces of the arms may be textured.

The sacral screw assembly may be inserted into a sacrum. In one procedure, the threaded shank of a fixation component is screwed into the sacrum at a desired location. A connector is snapped onto a spinal rod, and the connector is properly positioned within the cavity of the fixation component. The open top of the fixation component allows good visibility of the surgical site during placement and positioning of spinal rod and connector. A fastener may then be threaded onto the connector to attach the connector to the fixation component. Tightening the fastener securely fixes the position of the spinal rod relative to the fixation component, and tightening the fastener inhibits translational and rotational motion of the spinal rod. A second connector may be snapped onto the rod. The second connector may be used to attach the rod to a second fixation component or to a fixation device, such as a hook. The second connector may be positioned without detaching the rod from the fixation component, and without altering the position of any other connectors, fixation components, or fixation devices attached to the rod.

BRIEF DESCRIPTION OF THE DRAWINGS

Further advantages of the present invention will become apparent to those skilled in the art with the benefit of the following detailed description of the preferred embodiments and upon reference to the accompanying drawings in which:

FIGS. 2a–2c show views of an embodiment of a fixation component;

FIGS. 3a–3b show elevational views of an embodiment of a connector;

FIGS. 4a–4b show views of a spinal rod;

FIG. 5b shows a cross-sectional view taken substantially along line 5b–5b of FIG. 5a;

Figure 1:
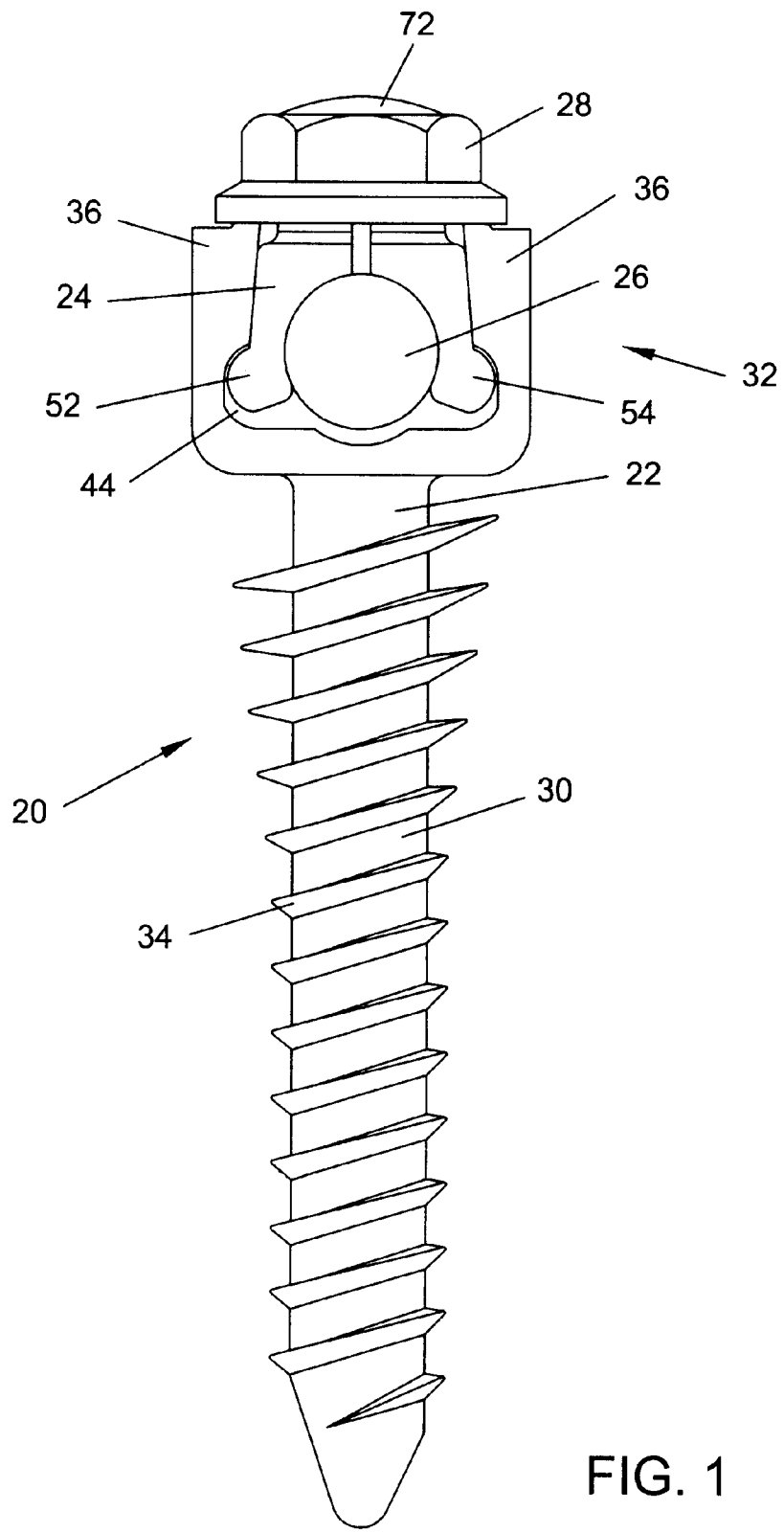
FIG. 1 shows an elevational view of an embodiment of a sacral screw assembly.
Figure 6A:
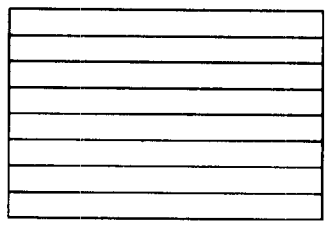
FIGS. 6a–6f shows various texturing patterns.
Figure 6B:
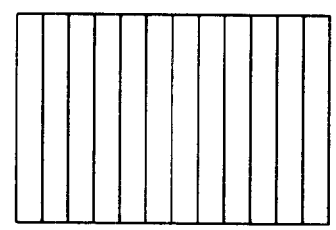
Figure 6C:
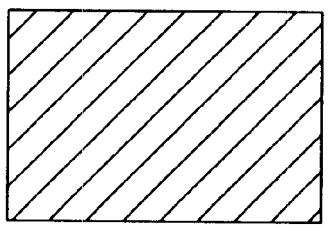
Figure 6D:
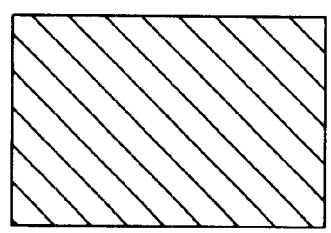
Figure 6E:
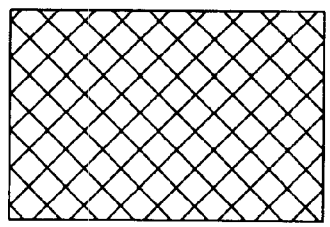
Figure 6F:
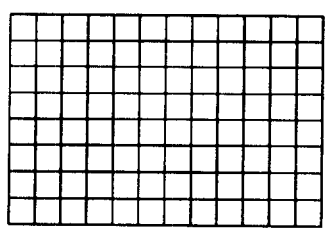

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

With reference to the drawings a sacral screw assembly is denoted generally as 20.

FIG. 1 shows a sacral screw assembly 20. FIGS. 2–5 show components of an embodiment of a sacral screw assembly 20. The components may include a fixation to component 22, connector 24, spinal rod 26, and fastener 28. The components of the sacral screw assembly 20 may be made of steel (e.g. stainless steel), steel alloys, titanium, or titanium alloys. These materials are generally nontoxic, biocompatible, strong and non-corrosive. Other materials that have these properties may also be used.

FIGS. 2a–2c show an embodiment of a fixation component 22. The fixation component 22 may have shank 30 and head 32. The shank 30 may be threaded with thread 34 that has a constant pitch. The pitch of the thread 34 may be constant regardless of the diameter of the shank 30 so that, if needed, a surgeon may remove a small diameter shank fixation component and replace it with a larger diameter shank fixation component. Because the pitch of the threading on the small diameter shank fixation component and the pitch of the threading on the large diameter shank fixation component are equal, the thread of the larger diameter shank fixation component will fit within the pattern cut by the thread of the small diameter shank fixation component. As shown in FIG. 2a, the shank 30 may have a substantially constant diameter, and the thread depth of the thread 34 may vary. The thread 34 may start near a tapered end of the shank 30 and may have a constant thread depth for a portion of the shank length. The thread depth may then be tapered so that the thread depth is greatest near the head 32 of the fixation component 22. The large thread depth proximate the head 32 may allow the fixation component 22 to provide better purchase in soft bone tissue. In an alternate embodiment (not shown), the thread depth may be constant throughout the length of the threaded portion of the fixation component 22.

The head 32 of the fixation component 22 may have walls 36, bottom 38, and arcuate wedges 40. The walls 36 and bottom 38 define a cavity 42. The walls 36 may be tapered so that the width between the walls is greatest near the bottom of the cavity 42 and least near the top of the cavity. Grooves 44 may be formed near the bottom 38 of the cavity 42. The bottom 38 may have optional rod groove 46 that complements the shape of the spinal rod 26. The rod groove 46 may allow the profile of the head 32 of the fixation component 22 to be short. Arcuate wedges 40 may be formed in the top of each wall 36. The arcuate wedges 40 may be engaged by a portion of the fastener 28 when the fastener is used to attach the connector 24 to the fixation component 22.

As shown in FIG. 2b, indentations 48 (only one shown) may be formed in the outer surfaces of the walls 36. An indentation 48 may serve as an anchoring point for an instrument (not shown) that aligns a connector 24 within the cavity 42. The connector 24 may need to be aligned so that the fastener 28 engages the wedges 40 of the fixation component 22 when the fastener is attached to the connector and tightened.

Indentation 50 in the bottom 38, as shown in FIG. 2c, may serve as an anchoring point for an instrument (not shown) that attaches to the fixation component 22. The instrument securely couples to the fixation component 22 and allows the fixation component to be driven into bone at a desired location.

FIGS. 3a and 3b show an embodiment of a connector 24. The connector 24 may have first arm 52, flared first arm tip 54, second arm 56, flared second arm tip 58, and threaded portion 60. Opening 62 may be formed between the first arm 52 and the second arm 54. The opening may be U-shaped.

A spinal rod 26 may be inserted into the opening 62 of the connector 24. The connector may have slot 64 between the first arm 52 and the second arm 56. The slot 64 may allow the arms 52, 56 to be deflected relative to each other. When the slot 64 narrows, the arms 52, 56 apply a compressive force against a rod 26 positioned in the opening 62 to securely hold the rod. When the slot 64 widens, the rod 26 positioned within the opening 62 may be moved or removed from the opening. For a cylindrically shaped spinal rod 26, the surfaces of the arms 52, 56 that contact the spinal rod may enclose more than π radians of the circumference of the rod, but less than 2π radians of the circumference of the rod. A connector 24 may be snapped onto a rod 26 by positioning the opening 62 of the connector over the rod and applying a downward force to the connector.

The connector 24 may be configured to be at least partially disposed within the cavity 42 of the fixation component 22 during use. The tapered inner surfaces of the cavity walls 36 may exert a compressive force onto tapered outer surfaces of the connector arms 52, 56 when a fastener 28 attaches the connector 24 to the fixation component 22. The compressive force exerted on the arms 52, 56 may serve to narrow the slot 64 of the connector 24. Narrowing the slot 64 may inhibit translational and rotational movement of a spinal rod 26 positioned within the opening 62 of the connector 24.

To further inhibit motion of the spinal rod 26, the surface of the spinal rod that contacts the arms 52, 56 may be textured. FIG. 4b shows a spinal rod that has textured surface 66 and non-textured surface 68. The non-textured surface of the spinal rod 26 may be inserted into a channel formed in the sacrum to provide a 'sacroiliac buttress.' The surfaces of the arms 52, 56 that contact the spinal rod 26 may be textured. Textured surfaces may have higher coefficients of friction than corresponding non-textured surfaces. Texturing the surface of the spinal rod 26 and/or the surface of the arms 52, 56 that contact the spinal rod may further inhibit motion of the spinal rod when the fastener 28 attaches the connector 24 to the fixation component 22. While it is preferred that the contact surface of the spinal rod 26 and the contact surfaces of the arms 52, 56 are textured, texturing of only one of the surfaces may be sufficient to attain additional resistance to movement.

In general, any process which transforms a relatively smooth surface into a roughened surface having an increased coefficient of friction may be used to texture a surface. Methods for forming a roughened surface include, but are not limited to: sanding, forming grooves within a surface, ball peening processes, electric discharge processes, and embedding of hard particles within a surface. In an embodiment a plurality of grooves may be formed in a surface. The grooves may be formed in a variety of patterns, such as the patterns depicted in FIGS. 6a–6f.

In an embodiment, a textured surface may be formed by an electrical discharge process. An electrical discharge process is based on the principle of removal of portions of a metal surface by spark discharges. Typically a spark is generated between the surface to be treated and an electrode by creating potential differential between the tool and the electrode. The spark produced tends to remove a portion of the surface disposed between the electrode and the surface. Typically, the electrode is relatively small such that only small portions of the surface are removed. By moving the electrode about the surface numerous cavities may be formed within the surface. Typically these cavities are somewhat pyramidal in shape. Various patterns may be formed within the surface depending on how the electrode is positioned during the discharge. A method for forming a frictional surface within a metal surface using an electric discharge process is described in U.S. Pat. No. 4,964,641 to Miesch et al., which is incorporated by reference as if set forth herein.

In an embodiment, a textured surface may be formed by a shot peening process. A shot peening process for forming a textured surface is described in U.S. Pat. No. 5,526,664 to Vetter which is incorporated by reference as if set forth herein. In general, a shot peening process involves propelling a stream of hardened balls, typically made of steel, at a relatively high velocity at a surface. To create a pattern upon an area of the surface the stream is typically moved about the surface. The speed by which the stream is moved about the surface tends to determine the type of textured surface formed.

In an embodiment, a textured surface may be formed by embedding sharp hardened particles in the surface. A method for embedding sharp hardened particles in a metal surface is described in U.S. Pat. No. 4,768,787 to Shira which is incorporated by reference as if set forth herein. The method of Shira involves using a laser or other high energy source to heat the surface such that the surface melts in selected areas. Just before the molten area resolidifies a stream of abrasive particles is directed to the area. In this manner some of the particles tend to become embedded with the molten surface. The particles typically have a number of sharp edges that protrude from the surface, after the particles have been embedded within the surface.

Any of the above methods of texturing may be used in combination with another method. For example, the outer surface of the spinal rod 26 may be textured using a pattern of grooves. The surfaces of the arms 52, 56, however, may be textured using an electrical discharge method. When coupled together the textured surfaces of the connector 24 and spinal rod 26 may interact with each other to provide additional resistance to translational and rotational movement.

Textured surfaces may also be formed on other contact surfaces of the components of the sacral screw assembly 20. In an embodiment, the walls 36 of the fixation component 22 may be textured. In an embodiment, the surfaces of the first arm 52 and the second arm 56 that contact the walls 36 may be textured. Textured components may be less susceptible to movement after the device has been implanted within a patient.

The first arm 52 and the second arm 56 may have flared tips 54, 58. The flared tips 54, 58 may be positioned in grooves 44 of the fixation component 22. The flared tips 54, 58 may allow for the easy placement and positioning of a connector 24 within the cavity 42 of a fixation component 22. The flared tips 54, 58 may also inhibit displacement of the connector 24 through the top of the cavity 42 prior to securing the connector to the fixation component 22 with the fastener 28.

The threaded portion 60 of the connector 24 may engage threading 70 of the fastener 28. The threaded portion 60 may have rounded top 72. As shown in FIG. 1, the rounded top 72 may prevent the formation of sharp edges near the fastener 28 and the rounded top when the fastener 28 is securely attached to the connector 24.

The fastener 28 may securely attach the connector 24 to the fixation component 22. In an embodiment, the fastener has ring 74. The ring 74 is shown in FIG. 5b. The ring 74 may have sloped surface 76. The sloped surface 76 may engage the arcuate wedges 40 of the fixation component 22 when the fastener 28 is securely coupled to the connector 24. Contacting the arcuate wedges 40 with the ring 74 may help to ensure that the fixation component 22, connector 24 and fastener 28 remain properly aligned during use of the sacral screw assembly 20. Contacting the arcuate wedges 40 with the ring 74 may inhibit flaring of the walls 36 due to the contact of the tapered surface of the walls with the tapered surfaces of the arms 52, 56 when the fastener 28 is used to secure the connector 24 to the fixation component 22.

Figure 7:
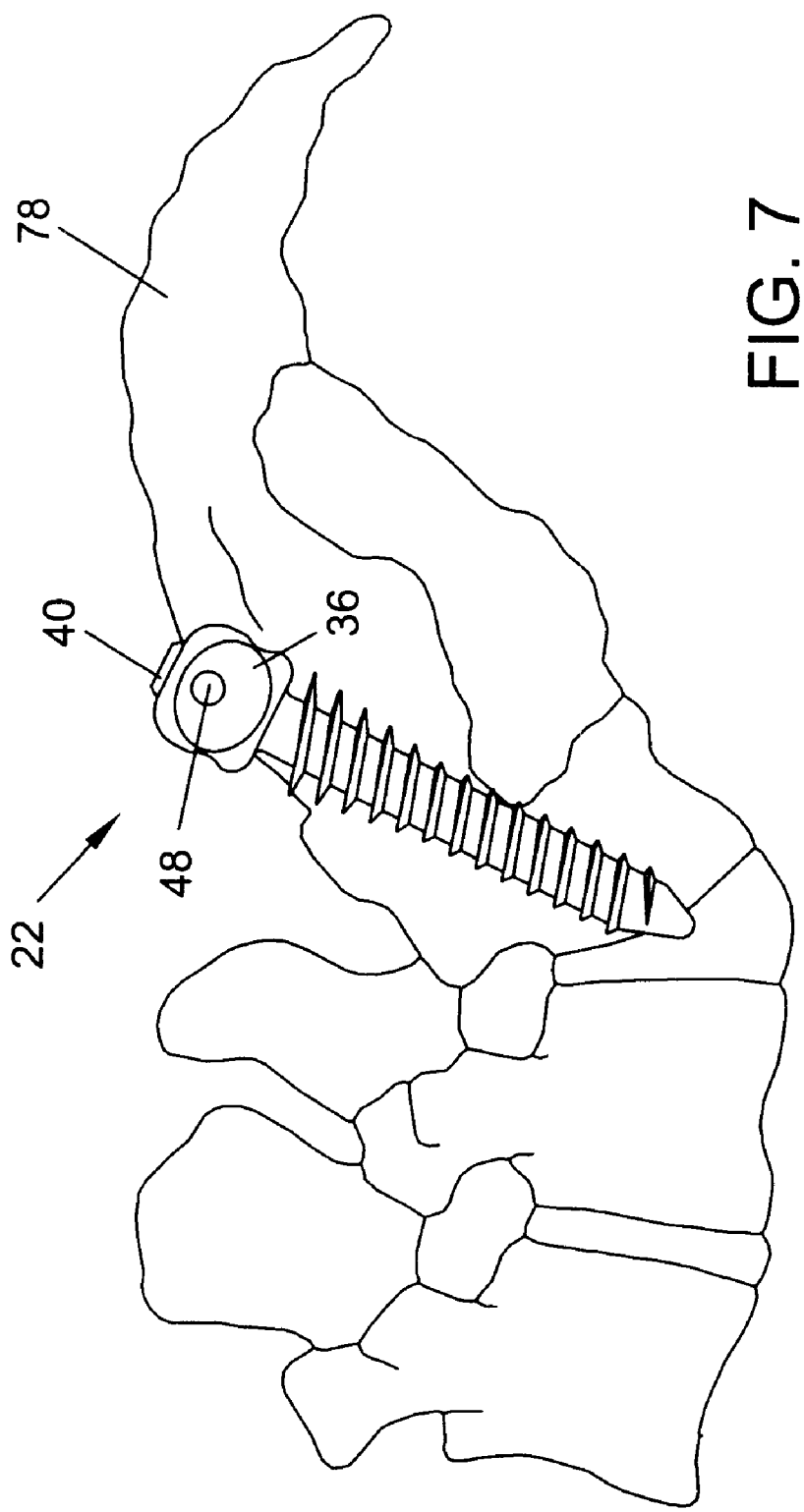
FIG. 7 is a diagrammatic representation of a fixation component inserted into a sacrum.

To use a sacral screw assembly 20, the fixation component 22 is inserted into sacrum 78 at a desired position. The fixation component 22 may enter the sacrum 78 at an oblique angle to inhibit backout of the fixation component 22 and to properly position the cavity 42 so that the spinal rod 26 will be properly oriented when positioned in the cavity. FIG. 7 shows a diagrammatic representation of a fixation component 22 inserted into the sacrum 72. A connector 24 is attached to a spinal rod 26 by snapping the opening 62 of the connector 24 onto the spinal rod. The connector 24 may be attached to the spinal rod 26 prior to insertion of the spinal rod into the surgical site, or after the insertion of the spinal rod into the surgical site. The connector 24 is able to slide along the length of the spinal rod 26 prior to attachment of the connector to the fixation component 22. The connector 24 is positioned at a desired location along the length of the spinal rod 26, and the connector is inserted into the cavity 42 of the fixation component 22. The fastener 28 is threaded onto the threaded portion 60 of the connector 24 so that the ring 74 of the fastener engages the arcuate wedges 40 of the fixation component 22. The fastener 28 is tightened to securely couple the connector 24 to the fixation component 22. Securing the fastener 28 to the connector 24 causes the walls 36 of the fixation component 22 to compress the arms 52, 56 of the connector against the spinal rod 26. The compression of the arms 52, 56 of the connector 24 narrows the slot 64 and fixes the connector to the spinal rod 26. Fixing the connector 24 to the spinal rod 26 inhibits translational and rotational motion of the spinal rod.

A second connector 24 may be snapped onto the rod 26. The second connector 24 may be used to attach the rod 26 to a second fixation component 22 or to a fixation device (not shown), such as a hook. The second connector 24 may be positioned without detaching the rod 26 from the fixation component 22, and without altering the position of any other connectors, fixation components, or fixation devices attached to the rod.

Figure 8:
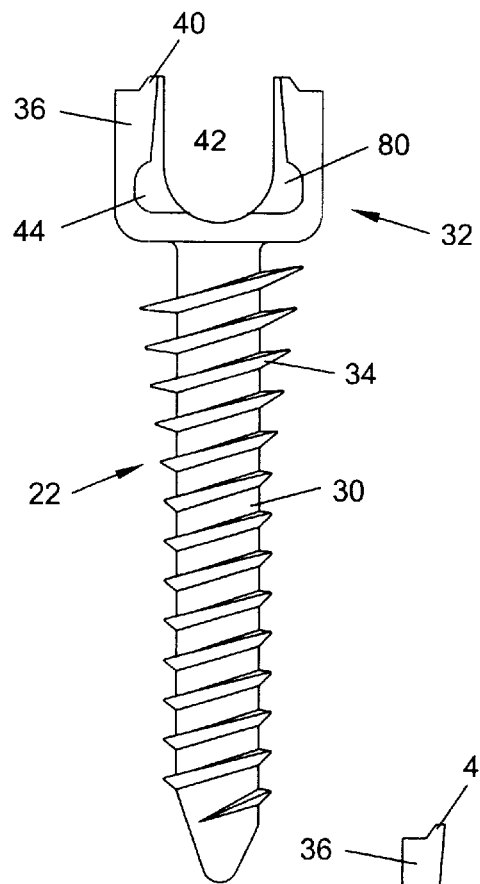
FIG. 8 is an elevational view of an embodiment of a fixation component having a connector stop.
Figure 9:
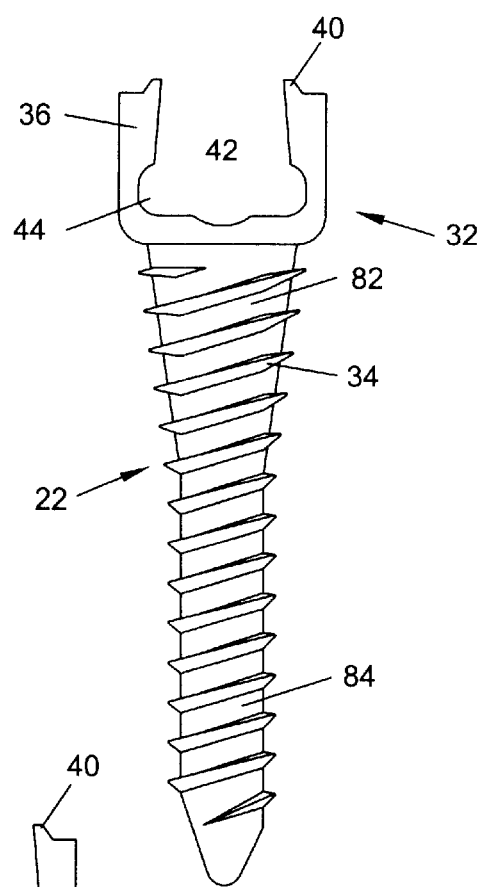
FIG. 9 is an elevational view of an embodiment of a fixation component having a variable diameter shank.
Figure 10:
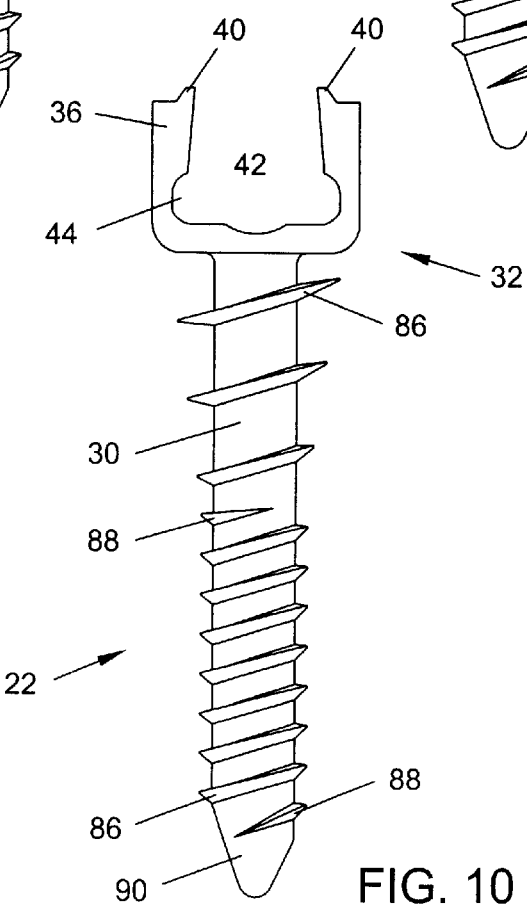
FIG. 10 is an elevational view of an embodiment of a fixation component having two flights of threads.

FIGS. 8–10 show alternate embodiments of fixation components 22. FIG. 8 shows an embodiment of a fixation component including connector stop 80. The connector stop 80 prevents a connector 24 from entering or exiting the cavity 42 from a particular side, but does not inhibit the passage of a spinal rod 26 through the cavity.

FIG. 9 shows a fixation component 22 with a variable diameter shank 30. The shank 30 has tapered portion 82 and constant diameter portion 84. The tapered portion 82 has a greatest diameter near the head 32.

FIG. 10 depicts a spinal fixation component 22 with a first threading 86 and a second threading 88. The first thread 86 extends from a position near end 90 of the shank 30 to a position near the head 32. The second thread 88 begins near the end 90 of the shank 30, but the second thread terminates a significant distance below the head 32. The pitch of the first thread 86 and the pitch of the second thread 88 may be constant. The pitch of the first thread 86 and the pitch of the second thread 88 may be equivalent so that the distance between the crest of a first thread and the crest of an adjacent second thread is half the length of the pitch. In the area of the shank 30 where the first thread 86 and the second thread 88 are intertwined, the distance between thread crests is smaller. The intertwined thread portion of the shank 30 effectively creates a fine pitch thread. The fine pitch thread section may allow the fixation component to provide better purchase in dense bone material. The threading that is proximate to the head 32 has a coarse pitch. The coarse pitch section of the shank 30 may allow the fixation component to provide better purchase in soft bone material. Having two flights of threads on the shank 30 of the fixation component 22 may help to minimize the chance of the fixation component backing out of a sacrum 78 into which the fixation component is threaded.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of implanting a sacral screw assembly, comprising:

connecting a shank of a fixation component to a portion of a spine, the fixation component comprising the shank and a head, wherein the head has an inner surface that forms a cavity;

placing a spinal rod into an opening of a connector;

positioning the connector and the rod within the cavity so that the inner surface engages a surface of the connector and a flared end of the connector resides within a groove in a cavity wall; and securing the connector to the fixation component.

2. The method of claim 1, wherein connecting a shank of a fixation component to a portion of a spine comprises screwing the shank into the portion of the spine.

3. The method of claim 1, wherein the shank further comprises threading, and wherein the threading on the shank comprises a fine pitch thread near an end of the shank, and a coarse pitch thread near the head.

4. The method of claim 1, further comprising placing a second connector onto the spinal rod after the spinal rod has been attached to the fixation component, the second connector being clamped onto the spinal rod without detaching the spinal rod from the fixation component and without altering a position of any other connectors engaged to the spinal rod.

5. The method of claim 1, wherein the spinal rod comprises a circumferential portion, and wherein the lower section of the connector surrounds greater than about $\pi$ radians of the circumferential portion and less than about $2\pi$ radians of the circumferential portion after the connector is positioned within the cavity.

6. The method of claim 1, further comprising applying a distraction force to the connector to change the location of the connector on the spinal rod.

7. The method of claim 1, further comprising removing a connector from the spinal rod after the spinal rod has been attached to the fixation component, the connector being removed without detaching the spinal rod from the fixation component and without altering a position of any other connectors engaged to the spinal rod.

8. A bone fixation system, comprising:
  a connector comprising a first arm and a second arm, the first arm and the second arm defining an opening, and a slot between the first arm and the second arm in communication with the opening;
  a fixation component comprising a head and a shank, the head having a base, a first wall and a second wall;
  a cavity formed by the first wall, the base, and the second wall, wherein the connector is configured to be at least partially disposed within the cavity during use;
  a groove in the cavity configured to receive an end of the first arm of said connector, and wherein the groove is configured to engage the end of the first arm to prevent removal of the connector through a top of the cavity; and
  a fastener configured to secure the connector to the fixation component.

9. The system of claim 8, wherein the fixation component comprises a back configured to inhibit passage of the connector through the cavity.

10. The system of claim 8, wherein a portion of an outer surface of the first arm and a portion of an outer surface of the second arm taper to complement a narrowing of the cavity from a bottom of the cavity to the top of the cavity.

11. The system of claim 8, wherein the connector comprises a threaded portion attached to the first and second arms, and wherein the fastener is configured to engage the threaded portion to secure the connector to the fixation component.

12. The system of claim 8, wherein a portion of an inner surface of the first arm comprises texturing.

13. The system of claim 8, wherein a portion of an outer surface of the first arm comprises texturing.

14. A bone fixation system, comprising:
  a connector comprising a first arm and a second arm, the first arm and the second arm defining an opening;
  a fixation component comprising a head and a shank, the head having a base, a first wall and a second wall, and wherein the first wall comprises an arcuate wedge;
  a cavity formed by the first wall, the base, and the second wall, wherein the connector is configured to be at least partially disposed within the cavity during use;
  a groove in the cavity configured to receive an end of the first arm of said connector, and wherein the groove is configured to engage the end of the first arm to prevent removal of the connector through a top of the cavity; and
  a fastener configured to secure the connector to the fixation component, wherein the fastener comprises a bottom section configured to engage the arcuate wedge.

15. The system of claim 14, wherein the fixation component comprises a back configured to inhibit passage of the connector through the cavity.

16. The system of claim 14, wherein a portion of an outer surface of the first arm and a portion of an outer surface of the second arm taper to complement a narrowing of the cavity from a bottom of the cavity to the top of the cavity.

17. The system of claim 14, wherein the connector comprises a threaded portion attached to the first and second arms, and wherein the fastener is configured to engage the threaded portion to secure the connector to the fixation component.

18. The system of claim 14, wherein a portion of an inner surface of the first arm comprises texturing.

19. The system of claim 14, wherein a portion of an outer surface of the first arm comprises texturing.

20. A bone fixation system, comprising:
  a connector comprising a first arm and a second arm, the first arm and the second arm defining an opening, and wherein a portion of an inner surface of the first arm is textured;
  a fixation component comprising a head and a shank, the head having a base, a first wall and a second wall;
  a cavity formed by the first wall, the base, and the second wall, wherein the connector is configured to be at least partially disposed within the cavity during use;
  a groove in the cavity configured to receive an end of the first arm of said connector, and wherein the groove is configured to engage the end of the first arm to prevent removal of the connector through a top of the cavity; and
  a fastener configured to secure the connector to the fixation component.

21. The system of claim 20, wherein the fixation component comprises a back configured to inhibit passage of the connector through the cavity.

22. The system of claim 20, wherein a portion of an outer surface of the first arm and a portion of an outer surface of the second arm taper to complement a narrowing of the cavity from a bottom of the cavity to the top of the cavity.

23. The system of claim 20, wherein the connector comprises a threaded portion attached to the first and second arms, and wherein the fastener is configured to engage the threaded portion to secure the connector to the fixation component.

24. The system of claim 20, wherein a portion of an outer surface of the first arm comprises texturing.

25. A bone fixation system, comprising:
  a connector comprising a first arm and a second arm, the first arm and the second arm defining an opening, and wherein a portion of an outer surface of the first arm is textured;
  a fixation component comprising a head and a shank, the head having a base, a first wall and a second wall;
  a cavity formed by the first wall, the base, and the second wall, wherein the connector is configured to be at least partially disposed within the cavity during use;
  a groove in the cavity configured to receive an end of the first arm of said connector, and wherein the groove is configured to engage the end of the first arm to prevent removal of the connector through a top of the cavity; and
  a fastener configured to secure the connector to the fixation component.

26. The system of claim 25, wherein the fixation component comprises a back configured to inhibit passage of the connector through the cavity.

27. The system of claim 25, wherein a portion of an outer surface of the first arm and a portion of an outer surface of the second arm taper to complement a narrowing of the cavity from a bottom of the cavity to the top of the cavity.

28. The system of claim 25, wherein the connector comprises a threaded portion attached to the first and second arms, and wherein the fastener is configured to engage the threaded portion to secure the connector to the fixation component.

29. A bone fixation system, comprising:
- a connector comprising a first arm and a second arm, said first arm and said second arm defining an opening;
- a fixation component comprising a head and a shank, the head having a base, a first wall and a second wall, and wherein the shank comprises a first thread flight and a second thread flight, wherein the first thread flight begins near an end of the shank and ends near the head, and wherein the second thread flight begins near an end of the shank and ends a significant distance from the end of the first thread flight;
- a cavity formed by the first wall, the base, and the second wall, wherein the connector is configured to be at least partially disposed within the cavity during use;
- a groove in the cavity configured to receive an end of the first arm of said connector, and wherein the groove is configured to engage the end of the first arm to prevent removal of the connector through a top of the cavity; and
- a fastener configured to secure the connector to the fixation component.

30. The system of claim 29, wherein the fixation component comprises a back configured to inhibit passage of the connector through the cavity.

31. The system of claim 29, wherein a portion of an outer surface of the first arm and a portion of an outer surface of the second arm taper to complement a narrowing of the cavity from a bottom of the cavity to the top of the cavity.

32. The system of claim 29, wherein the connector comprises a threaded portion attached to the first and second arms, and wherein the fastener is configured to engage the threaded portion to secure the connector to the fixation component.

33. The system of claim 29, wherein a portion of an inner surface of the first arm comprises texturing.

34. The system of claim 29, wherein a portion of an outer surface of the first arm comprises texturing.

35. A sacral fixation system, comprising:
- a connector comprising an opening, a flared end, and a slot in a portion of the connector in communication with the opening;
- a rod positionable within the opening, wherein the rod is fixable within the opening by a clamping force exerted by the connector during use;
- a fixation component comprising a head and a shank, the head comprising a cavity, wherein the connector is configured to be at least partially disposed within the cavity so that a surface of the cavity engages and exerts a compressive force on a surface of the connector to maintain the rod within the opening during use, wherein the flared end of the connector is configured to reside within a groove in a cavity wall, and wherein the slot of the connector is configured to allow the connector to deflect when the connector is positioned within the fixation component to secure the rod within the opening of the connector; and
- a fastener configured to couple the connector to the fixation component.

36. The system of claim 35, wherein the connector comprises texturing configured to engage the rod.

37. The system of claim 35, wherein the shank comprises threading.

38. A sacral fixation system, comprising:
- a connector comprising an opening and a flared end;
- a rod positionable within the opening, wherein the rod is fixable within the opening by a clamping force exerted by the connector during use;
- a fixation component comprising a head and a shank, the head comprising a cavity, a first wall and a second wall, wherein the connector is configured to be at least partially disposed within the cavity so that a surface of the cavity engages and exerts a compressive force on a surface of the connector to maintain the rod within the opening during use, and wherein the flared end of the connector is configured to reside within a groove in a cavity wall;
- a first protrusion on a top of the first wall and a second protrusion on a top of the second wall; and
- a fastener configured to couple the connector to the fixation component, wherein a portion of the fastener is configured to engage the first protrusion and the second protrusion when the fastener couples the connector to the fixation component.

39. The system of claim 38, wherein the fixation component comprises a back configured to inhibit passage of the connector through the cavity.

40. The system of claim 38, wherein a portion of an inner surface defining the opening comprises texturing.

41. A sacral fixation system, comprising:
- a connector comprising an opening and a flared end;
- a rod positionable within the opening, wherein the rod is fixable within the opening by a clamping force exerted by the connector during use;
- a fixation component comprising a head and a shank, the head comprising a cavity, wherein the connector is configured to be at least partially disposed within the cavity so that a surface of the cavity engages and exerts a compressive force on a surface of the connector to maintain the rod within the opening during use, and wherein the flared end of the connector is configured to reside within a groove in a cavity wall;
- a fastener configured to couple the connector to the fixation component; and
- texturing on a portion of the fixation component that is configured to contact the connector.

42. The system of claim 41, wherein the fixation component comprises a back configured to inhibit passage of the connector through the cavity.

43. The system of claim 41, wherein the head comprises a plurality of protrusions configured to engage a portion of the fastener when the fastener couples the connector to the fixation component.

44. A sacral fixation system, comprising:
- a connector comprising an opening and a flared end, wherein a portion of an inner surface of the connector that defines the opening is textured;
- a rod positionable within the opening, wherein the rod is fixable within the opening by a clamping force exerted by the connector during use;
- a fixation component comprising a head and a shank, the head comprising a cavity, wherein the connector is configured to be at least partially disposed within the cavity so that a surface of the cavity engages and exerts a compressive force on a surface of the connector to maintain the rod within the opening during use, and wherein the flared end of the connector is configured to reside within a groove in a cavity wall; and
- a fastener configured to couple the connector to the fixation component.

45. The system of claim 44, wherein the fixation component comprises a back configured to inhibit passage of the connector through the cavity.

46. The system of claim 44, wherein the head comprises a plurality of protrusions configured to engage a portion of the fastener when the fastener couples the connector to the fixation component.

47. A sacral fixation system, comprising:
a connector comprising an opening and a flared end;
a rod positionable within the opening, wherein the rod is fixable within the opening by a clamping force exerted by the connector during use;
a fixation component comprising a head and a shank, the head comprising a cavity, wherein the connector is configured to be at least partially disposed within the cavity so that a surface of the cavity engages and exerts a compressive force on a surface of the connector to maintain the rod within the opening during use, and wherein the flared end of the connector is configured to reside within a groove in a cavity wall;
a fastener configured to couple the connector to the fixation component; and
texturing on a portion of the connector that is configured to contact a portion of the fixation component cavity that defines the cavity.

48. The system of claim 47, wherein the fixation component comprises a back configured to inhibit passage of the connector through the cavity.

49. The system of claim 47, wherein the head comprises a plurality of protrusions configured to engage a portion of the fastener when the fastener couples the connector to the fixation component.

50. A sacral fixation system, comprising:
a connector comprising an opening and a flared end;
a rod positionable within the opening, wherein the rod is fixable within the opening by a clamping force exerted by the connector during use;
a fixation component comprising a head and a shank, the head comprising a cavity, wherein the connector is configured to be at least partially disposed within the cavity so that a surface of the cavity engages and exerts a compressive force on a surface of the connector to maintain the rod within the opening during use, and wherein the flared end of the connector is configured to reside within a groove in a cavity wall;
a fastener configured to couple the connector to the fixation component; and
wherein the shank comprises a first thread flight and a second thread flight, wherein the first thread flight begins near an end of the shank and ends near the head, and wherein the second thread flight begins near an end of the shank and ends a significant distance from the end of the first thread flight.

51. The system of claim 50, wherein the fixation component comprises a back configured to inhibit passage of the connector through the cavity.

52. The system of claim 50, wherein the head comprises a plurality of protrusions configured to engage a portion of the fastener when the fastener couples the connector to the fixation component.

53. A fixation component of a sacral fixation system, comprising:
a head;
a cavity in the head, the cavity formed between a first wall, a base, and a second wall;
a groove in the head, the groove configured to mate to an end of a connector to inhibit passage of the connector through a top of the cavity; and
a shank coupled to the head, the shank comprising a first thread flight and a second thread flight, wherein the first thread flight begins near an end of the shank and ends near the head, and wherein the second thread flight begins near an end of the shank and ends a significant distance from the end of the first thread flight.

54. The fixation component of claim 53, wherein the head comprises a back configured to inhibit passage of the connector through the cavity.

55. The system of claim 53, wherein the head comprises a plurality of protrusions configured to engage a portion of the fastener when the fastener couples the connector to the fixation component.

56. A fixation component of a sacral fixation system, comprising:
a head;
a cavity in the head, the cavity formed between a first wall, a base, and a second wall;
a groove in the head, the groove configured to mate to an end of a connector to inhibit passage of the connector through a top of the cavity;
a shank coupled to the head; and
texturing on a portion of a surface of the head that is configured to contact the connector.

57. The system of claim 56, wherein the head comprises a back configured to inhibit passage of the connector through the cavity.

58. The system of claim 56, wherein the head comprises a plurality of protrusions configured to engage a portion of the fastener when the fastener couples the connector to the fixation component.

59. A fixation component of a sacral fixation system, comprising:
a head;
a cavity in the head, the cavity formed between a first wall, a base, and a second wall;
a groove in the head, the groove configured to mate to an end of a connector to inhibit passage of the connector through a top of the cavity;
a shank coupled to the head;
a wedge on a top of the first wall, wherein a portion of a fastener is configured to engage the wedge when the fastener attaches the connector to the fixation component.

60. The fixation component of claim 59, wherein the head comprises a back configured to inhibit passage of the connector through the cavity.

61. A connector of a sacral fixation system, comprising:
an upper section;
a first arm coupled to the upper section;
a flared tip at an end of the first arm, the flared tip configured to reside within a cavity of a fixation component during use;
a second arm coupled to the upper section; and
an opening between the first arm and the second arm, the opening configured to couple the connector to a spinal rod, wherein a surface of the connector that forms the opening comprises texturing.

62. The connector of claim 61, wherein a surface of the first arm configured to contact a surface of the fixation component defining the cavity comprises texturing.

63. A connector of a sacral fixation system, comprising:
an upper section;
a first arm coupled to the upper section;

a flared tip at an end of the first arm, the flared tip configured to reside within a cavity of a fixation component during use;

a second arm coupled to the upper section;

an opening between the first arm and the second arm, the opening configured to couple the connector to a spinal rod; and wherein a portion of a surface of the connector that is configured to contact walls of a cavity of a fixation component comprises texturing.

64. The connector of claim 63, wherein a surface of the connector that forms the opening comprises texturing.

* * * * *